United States Patent [19]

Daum et al.

[11] 4,396,609
[45] Aug. 2, 1983

[54] AMINOCYCLITOL ANTIBIOTICS, PHARMACEUTICAL COMPOSITIONS AND METHOD OF USING SAME

[75] Inventors: Sol J. Daum, Albany; Robert L. Clarke, Bethlehem, both of N.Y.

[73] Assignee: Sterling Drug Inc., New York, N.Y.

[21] Appl. No.: 830,393

[22] Filed: Sep. 6, 1977

Related U.S. Application Data

[60] Continuation-in-part of Ser. No. 761,907, Jan. 24, 1977, abandoned, which is a continuation-in-part of Ser. No. 739,246, Nov. 5, 1976, abandoned, which is a division of Ser. No. 651,034, Jan. 21, 1976, Pat. No. 4,028,188, which is a division of Ser. No. 550,273, Feb. 18, 1975, Pat. No. 3,972,930.

[51] Int. Cl.$^3$ .................... A61K 31/71; C07H 15/22
[52] U.S. Cl. .................................. 424/180; 536/13.6; 536/16.8; 435/80
[58] Field of Search .............................. 536/17, 13.6

[56] References Cited

U.S. PATENT DOCUMENTS 3,669,838  6/1972  Shier et al. ................... 536/16.8
3,780,018 12/1973  Konishi et al. ................ 536/17
3,796,699  3/1974  Naito et al. ................... 536/17
3,828,021  8/1974  Beattie et al. ................. 536/17
4,053,591 10/1977  Daniels et al. ................ 536/13.6

FOREIGN PATENT DOCUMENTS 1364521  8/1974  United Kingdom .............. 536/13.6

OTHER PUBLICATIONS

Cooper et al., "J. Chem. Soc.", 1971, pp. 2876–2879.

Primary Examiner—Johnnie R. Brown
Attorney, Agent, or Firm—William G. Webb; B. Woodrow Wyatt

[57] ABSTRACT

Aminocyclitol analogs of gentamicin $C_1$, $C_2$ and $C_{1a}$ and the corresponding compounds acylated on the 1-, 3- and 2'-amino groups with an $\omega$-amino-$\alpha$-hydroxy-lower-alkanoyl group are prepared by culturing a nutrient medium containing carbohydrates, a source of assimilable nitrogen, essential salts and an added aminocyclitol with a mutant of *Micromonospora purpurea* and acylating the product with an ester of an $\omega$-(N-benzyloxycarbonyl)amino-$\alpha$-hydroxy-lower-alkanoic acid followed by catalytic hydrogenolysis of the benzyloxycarbonyl group.

24 Claims, No Drawings

AMINOCYCLITOL ANTIBIOTICS, PHARMACEUTICAL COMPOSITIONS AND METHOD OF USING SAME

RELATED APPLICATIONS

This is a continuation-in-part of our prior, copending application Ser. No. 761,907, filed Jan. 24, 1977, now abandoned, which in turn is a continuation-in-part of our prior copending application Ser. No. 739,246, filed Nov. 5, 1976, now abandoned, which in turn is a division of our prior application Ser. No. 651,034, filed Jan. 21, 1976, copending with said application Ser. No. 739,246, and now U.S. Pat. No. 4,028,188, patented June 7, 1977, said application Ser. No. 651,034 in turn being a division of our prior application Ser. No. 550,273, filed Feb. 18, 1975, copending with said application Ser. No. 651,034, and now U.S. Pat. No. 3,972,930, patented Aug. 3, 1976.

BACKGROUND OF THE INVENTION (a) Field of the Invention

This invention relates to aminocyclitol antibiotics of the gentamicin type useful as antibacterial agents.

(b) Description of the Prior Art

The gentamicin complex of antibiotics produced by *Micromonospora purpurea* is known to consist primarily of three components designated $C_1$, $C_2$ and $C_{1a}$ having the structures

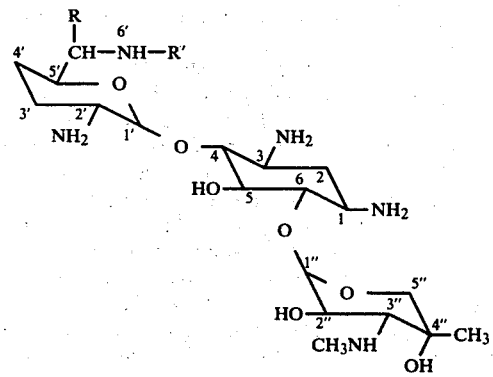

Gentamicin $C_1$: R = R' = $CH_3$
Gentamicin $C_2$: R = $CH_3$, R' = H
Gentamicin $C_{1a}$: R = R' = H (Cooper et al. J. Chem Soc., Sect. C, 1971, 2876–2879; Konishi et al. U.S. Pat. No. 3,780,018, patented Dec. 18, 1973; British Pat. No. 1,364,521, published Aug. 21, 1974; and Merck Index, Eighth Edition, page 485), and the 1-, 3- and 2'-(γ-amino-α-hydroxybutyryl) analogs of gentamicin $C_1$ are also known (Konishi et al., loc. cit.).

Moreover, it is known that certain aminocyclitol-type antibiotics can be prepared by culturing microorganism mutants in a medium containing carbohydrates, a source of assimilable nitrogen, essential salts and an aminocyclitol subunit, which is incorporated by the organism into the antibiotic (Shier et al., U.S. Pat. No. 3,669,838, patented June 13, 1972). In the case of the gentamicin complex of compounds, which are each derivatives of deoxystreptamine, the added aminocyclitol subunit in the Shier et al. process is deoxystreptamine.

SUMMARY OF THE INVENTION

In a composition of matter aspect, the present invention relates to certain aminocyclitol analogs of gentamicin $C_1$, $C_2$ and $C_{1a}$ which are described chemically as O-[3-deoxy-4-C-methyl-3-methylamino-β-L-arabinopyranosyl-(1→6)]-O-[2-amino-6-amino(and 6-C-methyl and 6-methylamino-6-C-methyl)-2,3,4,6-tetradeoxy-α-D-erythro-glucopyranosyl-(1→4)]-streptamines. The invention also relates to the corresponding compounds acylated at one of the 1-, 3- and 2'-amino groups with a γ-amino-α-hydroxybutyryl or β-amino-α-hydroxypropionyl group.

In a process aspect, the invention relates to a process for preparing O-[3-deoxy-4-C-methyl-3-methylamino-β-L-arabinopyranosyl-(1→6)]-O-[2-amino-6-amino (and 6-C-methyl- and 6-methylamino-6-C-methyl)-2,3,4,6-tetradeoxy-α-D-erythro-glucopyranosyl-(1→4)]streptamines acylated on one of the 1-, 3- or 2'-amino groups with an ω-amino-α-hydroxy-loweralkanoyl group comprising reacting an O-[3-deoxy-4-C-methyl-3-methylamino-β-L-arabinopyranosyl-(1→6)]-O-[2-amino-6-amino- (and 6-C-methyl and 6-methylamino-6-C-methyl)-2,3,4,6-tetradeoxy-α-D-erythro-glucopyranosyl-(1→4)]streptamine with an N-hydroxysuccinimide ester of an ω-(N-benzyloxycarbonyl)amino-α-hydroxy-lower-alkanoic acid and hydrogenolysis of the benzyloxycarbonyl group in the resulting product with hydrogen over a catalyst.

DETAILED DESCRIPTION INCLUSIVE OF THE PREFERRED EMBODIMENTS

More specifically, this invention relates to compounds having the formula:

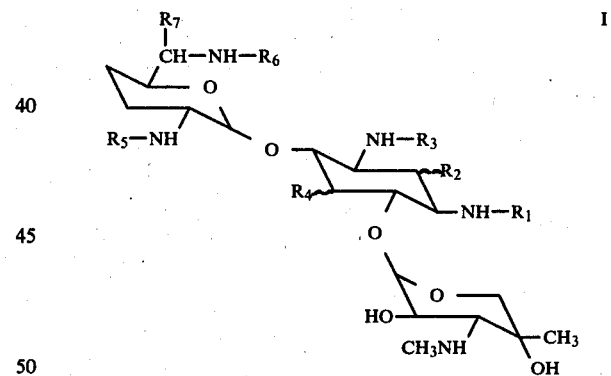

where $R_1$, $R_3$ and $R_5$ each represent hydrogen, or one of $R_1$, $R_3$ and $R_5$ represents an ω-amino-α-hydroxy-lower-alkanoyl group having the formula:

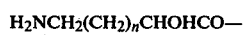

$H_2NCH_2(CH_2)_nCHOHCO-$ where n is zero or 1, the other of $R_1$, $R_3$ and $R_5$ being hydrogen; $R_2$ represents hydrogen or hydroxy; $R_4$ represents hydrogen, hydroxy or halogen (including fluorine, chlorine, bromine and iodine), except that when $R_2$ is hydrogen, $R_4$ is not hydroxy cis to the amino groups at the 1- and 3-positions; and $R_6$ and $R_7$ each represent hydrogen or methyl. The same nomenclature used to identify the various components of gentamicin according to the specific identities of the $R_6$ and $R_7$ groups is used herein to identify the compounds of the present invention, i.e.:

Component C$_1$: R$_6$=R$_7$=CH$_3$
Component C$_2$: R$_6$=H, R$_7$=CH$_3$
Component C$_{1a}$: R$_6$=R$_7$=H.

The compounds of formula I where R$_1$, R$_3$ and R$_5$ are hydrogen and R$_2$, R$_4$, R$_6$ and R$_7$ have the meanings given above are prepared by the method described in Shier et al. U.S. Pat. No. 3,669,838. This method comprises culturing a nutrient medium containing carbohydrates, a source of assimilable nitrogen, essential salts and an added aminocyclitol derivative having the formula:

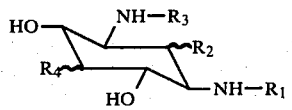

where R$_1$, R$_2$, R$_3$ and R$_4$ have the meanings given above, and where R$_1$ and R$_3$ can in addition represent a single bond joining the two nitrogen atoms together, and a mutant of *Micromonospora purpurea*, designed *Micromonospora purpurea* ATCC 31,119, and isolating the product from the culture medium. The compounds of formula I where both R$_1$ and R$_3$ are hydrogen are produced when the aminocyclitol of formula II where R$_1$ and R$_3$ represent a single bond is used. In accordance with the procedure described by Shier et al., the nature of the mutant is such that it is incapable of synthesizing the aminocyclitol subunit from a nutrient medium to thereby produce the antibiotic, but is capable of incorporating the latter into an antibiotic when the aminocyclitol is added to the nutrient medium.

The compounds of formula I, where one of R$_1$, R$_3$ and R$_5$ represents an ω-amino-α-hydroxy-lower-alkanoyl group, are prepared by the method described by Konishi et al., U.S. Pat. No. 3,780,018 which comprises reacting the compounds of formula I where each of R$_1$, R$_3$ and R$_5$ is hydrogen with an N-hydroxysuccinimide ester having the formula:

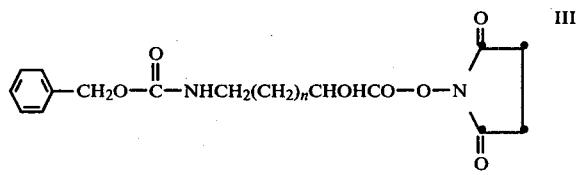

where n has the meanings given above. The resulting mixture of the compounds of formula I where one of R$_1$, R$_3$ and R$_5$ is the ω-(N-benzyloxycarbonyl)amino-α-hydroxy-lower-alkanoyl group:

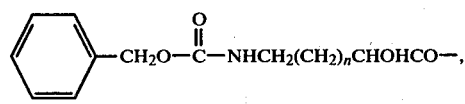

the other two being hydrogen, is then subjected to hydrogenolysis of the benzyloxycarbonyl group with hydrogen over a catalyst.

As indicated above, when a compound of formula I where each of R$_1$, R$_3$ and R$_5$ is hydrogen is used as starting material in the acylation reaction, a mixture of the three possible isomeric mono-amides is obtained in which one of the R$_1$, R$_3$ or R$_5$ amine hydrogen atoms is replaced by the ω-(N-benzyloxycarbonyl)amino-α-hydroxy-lower-alkanoyl group. When individual characterization and study of these products are desired, they must of course be separated from one another. The acylation reaction is carried out by reacting molar equivalent amounts of the compound of formula I and the N-hydroxysuccinimide ester, preferably at a temperature from −10° C. to about 10° C., and in an aqueous solution of an inert organic solvent, for example tetrahydrofuran, dioxane, ethylene glycol, dimethyl ether, dimethylacetamide, dimethylformamide, propylene glycol dimethyl ether and the like.

Hydrogenolysis of the benzyloxycarbonyl group is carried out over a palladium-on-charcoal catalyst in an inert, water miscible organic solvent, for example methanol, ethanol, dioxane, tetrahydrofuran, ethylene glycol dimethyl ether, propylene glycol dimethyl ether and the like.

The aminocyclitols of formula II where R$_1$, R$_2$ and R$_3$ are hydrogen and R$_4$ is fluorine or iodine are novel compounds, which are covered by U.S. Pat. No. 3,972,930, patented Aug. 3, 1976, and are prepared as described hereinbelow. Other aminocyclitols of formula II, which are also useful in the practice of the present invention, are known compounds. These are:
streptamine sulfate [Peck et al., J. Am. Chem. Soc. 68, 776 (1946)];
2-epistreptamine dihydrochloride [Suami et al., J. Org. Chem. 33, 2831 (1968)];
2,5-dideoxystreptamine dihydrochloride, m.p.>300° C.; and
6,7-diazabicyclo[3.2.1]octane-2,4-diol (exo, exo), m.p. 185°-193° C. [Both the latter two compounds disclosed by Testa et al., J. Antibiotics 27, 917-921 (1974)].

The N-hydroxysuccinimide esters of formula III are a generally known class of compounds.

Due to the presence of a basic amino grouping, the free base form represented by formula I above reacts with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, glyconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephosphonic acid, acidic resins, hydrofluoric acid, hydrochloric acid, hydrobromic acid, hydriodic acid, perchloric acid, nitric acid, sulfuric acid, phosphoric acid, arsenic acid, and the like.

All of the acid-addition salts are useful as sources of the free base forms, by reaction with an inorganic base. It will thus be appreciated that if one or more of the characteristics, such as solubility, molecular weight, physical appearance, toxicity, or the like of a given base or acid-addition salt thereof render that form unsuitable for the purpose at hand, it can be readily converted to another, more suitable form. For pharmaceutical purposes, acid-addition salts of relatively non-toxic, pharmaceutically-acceptable acids, for example, sulfuric acid, hydrochloric acid, lactic acid, tartaric acid, and the like, are of course employed.

The compounds of formula I have been tested in a standard serial dilution antibacterial test and have been found to have antibacterial activity, particularly against gentamicin resistant organisms. The compounds are thus useful as antibacterial agents.

The compounds of formula I are primarily intended for oral, topical or parenteral administration and can be prepared for use by suspension, either in the form of their free bases or as pharmaceutically acceptable, non-toxic acid addition salts, in an inert carrier such as polyethylene glycol, or by tabletting or encapsulation for oral administration either alone or with suitable adjuvants, or alternatively they can be formulated with conventional creams or jellies for topical application.

The molecular structures of the compounds of the invention were assigned on the basis of their method of preparation, and study of their chromatographic characteristics determined by their thin layer chromatographic (tlc) analyses; their nuclear magnetic resonance (nmr) and mass spectra; by degradation to known compounds; and by the correspondence between calculated and found values for elementary analyses for the elements.

The following specific examples are illustrative of the manner of making the compounds of the invention without being limited thereto.

PREPARATION OF NOVEL STREPTAMINES

Preparation 1

2-Deoxy-1,6:3,4-dicarbonylstreptamine [Umezawa et al. Bull. Chem. Soc. (Jap.) 44, 1411–1415 (1971)] (47 g., 0.21 mole) was suspended in 500 ml. of pyridine and the stirred suspension treated with 45 ml. of methanesulfonyl chloride. After cooling, the mixture was diluted with about 3 liters of methanol and the product filtered and dried to give 39 g. of 2-deoxy-5-methanesulfonyl-1,6:3,4-dicarbonylstreptamine, m.p. 264°–266° C.

A mixture of 2 g. (0.0069 mole) of 2-deoxy-5-methanesulfonyl-1,6:3,4-dicarbonylstreptamine, described above, and 4.8 g. (0.032 mole) of sodium iodide in 70 ml. of dimethylformamide was heated at 125° C. for twenty-four hours and then taken to dryness. The crude 2,5-dideoxy-5-iodo-1,6:3,4-dicarbonylstreptamine was mixed with 30 ml. of 6 N hydrochloric acid, the mixture refluxed for two and a half hours and then cooled and evaporated to dryness in vacuo. The crude 2,5-dideoxy-5-iodostreptamine dihydrochloride was dissolved in 30 ml. of acetic anhydride, the solution treated with 5.25 g. of sodium acetate and the mixture refluxed for two and half hours. The mixture was then cooled, poured into 200 ml. of water and extracted with chloroform. The chloroform extracts, on washing once with sodium thiosulfate solution, once with brine, once with water and evaporation to dryness, afforded an oil which was crystallized from ethanol to give two crops totaling 1.1 g. of N,N'-diacetyl-2,5-dideoxy-5-iodostreptamine, m.p. 256°–258° C. Hydrolysis of the latter by refluxing with aqueous hydrochloric acid and isolation from a basic medium affords 2,5-dideoxy-5-iodostreptamine.

Preparation 2

2-Deoxy-5-methanesulfonyl-1,6:3,4-dicarbonylstreptamine (39 g., 0.12 mole), described in Preparation 1 above, was suspended in approximately 200 ml. of 6 N hydrochloric acid, the mixture warmed on a steam bath for two hours, evaporated to dryness in vacuo, mixed with 200 ml. of isopropyl alcohol and evaporated to dryness once again. The residual oil was triturated with methanol, cooled and the solid collected and recrystallized from methanol to give 2-deoxy-5-methanesulfonylstreptamine dihydrochloride, m.p. 208°–210° C.

Anal. Calcd. for $C_7H_{16}N_2O_5S.2HCl$: C,26.84; H,5.79; N,8.94. Found: C,26.77; H,5.76; N,9.17.

A solution of 28.7 g (0.09 mole) of 2-deoxy-5-methanesulfonylstreptamine in 45 ml. of water and 90 ml. of 2 N sodium hydroxide was cooled in an ice bath and treated dropwise with stirring with a solution of 45 ml. of benzyl chloroformate in 80 ml. of toluene added from one dropping funnel and with 160 ml. of 2 N sodium hydroxide from another. When addition was complete, the mixture was stirred for an additional fifteen minutes, diluted with about 50 ml. of toluene, stirred for three hours and filtered. Recrystallization of the solid from ethanol afforded 4.0 g. of N,N'-dicarbobenzoxy-2-deoxy-5-methanesulfonylstreptamine, m.p. 198°–201° C.

Anal. Calcd. for $C_{23}H_{28}N_2O_9S$: C,54.32; H,5.55; N,5.51. Found: C,54.75; H,5.61; N,5.60.

Reaction of the latter with potassium fluoride in benzene or acetonitrile containing a crown either, e.g. 1,4,7,10,13,16-hexaoxacyclooctadecane, using the procedure described by Liotta et al., J. Am. Chem. Soc. 96, 2250–2252 (1974) affords N,N'-dicarbobenzoxy-2,5-dideoxy-5-fluorostreptamine which, on hydrolysis with aqueous mineral acid, affords 2,5-dideoxy-5-fluorostreptamine.

Mutation Process

In the following procedures various media constituted as follows were employed.

|  | g./l. |
| --- | --- |
| Medium 1: N—Z Amine | |
| Glucose | 10g. |
| Soluble starch | 20g. |
| Yeast extract | 5g. |
| N—Z—Amine-Type A (Difco) | 5g. |
| $CaCO_3$ | 1g. |
| Agar | 15g. |
| Medium 2: Germination Medium (in distilled water) | |
| Beef extract | 0.3% |
| Tryptone | 0.5% |
| Dextrose | 0.1% |
| Soluble starch | 2.4% |
| Yeast extract | 0.5% |
| $CaCO_3$ | 0.4% |
| Medium 3: Soybean-Glucose | |
| Soybean meal | 30g. |
| Dextrose (cerelose) | 40g. |
| $CaCO_3$ | 1g. |

| | g./l. |
|---|---|
| Medium 4: TGE | |
| Trypticase glucose extract | 5.0g. |
| Trypticase peptone | 3.0g. |
| Glucose | 1.0g. |
| Agar | 15.0g. |

The organism *Micromonospora purpurea* was obtained from the U.S. Dept. of Agriculture as NRRL 2953 and maintained on N-Z amine slants (medium 1). Submerged fermentations were conducted in flasks containing germination medium 2 for four days at 37° C. on a rotary shaker. From this first stage seed, a 10% inoculum was transferred to the germination medium (medium 2), and fermentation was continued as above at 28° C. for seven days.

For purposes of establishing the capability of the organism to biosynthesize gentamicin in the absence of added deoxystreptamine, a third stage fermentation using a 5% inoculum was carried out in a 10 liter fermentor in a soybean-glucose medium (3) at 28° C., agitating at 200 rpm and sparging at 2 liters/minute with filtered air. After six days, the tank contents were acidified to pH 2.0 with 6 N sulfuric acid, filtered, and a 500 ml. portion neutralized with ammonium hydroxide and passed through an IRC-50 ion exchange resin (Na+ form). The column was then rinsed with water and eluted with 2 N sulfuric acid. Following the procedure described in U.S. Pat. No. 3,091,572, there was isolated a 300 mg. sample of crude gentamicin, which was found to be biologically active and which contained three components similar to gentamicin $C_1$, $C_2$ and $C_{1a}$ by TLC examination.

For purposes of mutating the organism, broth cultures were cultivated in medium 2 (37° C. for three days) and the resultant cells harvested by centrifugation, washed and resuspended in buffered saline. This suspension was treated with the mutagenic agent, N-methyl-N'-nitro-N-nitrosoguanidine. Samples of the mutagenized culture were plated in medium 4 at 37° C. until colonies were evident (usually about one week). Colonies were picked to duplicate plates (medium 4), one set of which was overlaid with a spore suspension of *B. subtilis*. After incubation at 37° C. for from eighteen to twenty hours, the "picks" which showed no zone of inhibition on the *B. subtilis* plate were transferred from the master plate (no *B. subtilis*) to medium 1 slants and incubated until full growth was evident.

These potential nonproducing mutants were then challenged with deoxystreptamine in an attempt to stimulate antibiotic biosynthesis as follows. Stock cultures of the potential mutants were streaked as bands on the surface of medium 4 plates and incubated at 37° C. until growth was evident (about three to four days). Filter paper discs were then dipped into a solution of deoxystreptamine (500 mcg./ml.) and placed on top of the culture streak. After incubation for twenty-four hours, the surface of the plate was inoculated with *B. subtilis* using the overlay technique, and incubation was continued for an additional eighteen to twenty hours. Isolates showing zones of inhibition surrounding the disc were designated as deoxystreptamine mutants. One such mutant, coded VIB and deposited with the American Type Culture Collection, 12301 Parklawn Drive, Rockville, Md. 20852 as *Micromonospora purpurea* ATCC 31,119, was used for the production of the gentamicin-type antibiotics as described below.

BIOSYNTHESIS OF ANTIBIOTICS WITH MUTANT VIB

EXAMPLE 1

The mutant organism was maintained on N-Z amine agar slants (medium 1) from which transfers to flasks containing 500 ml. of germination medium 2 were made. The flasks were incubated at 28° C. for four days on a rotary shaker (2" stroke) at 225 rpm.

A 10% (v/v) inoculum from the germination stage was aseptically transferred to 14 liter fermentors containing 9 liters of sterile germination medium 2. These were agitated at 450 rpm at 28°–29° C. and sparged with filtered air at 5 liters/minute. At time of inoculation, 200 mg./liter of streptamine sulfate was added as a suspension in sterile distilled water. Fermentation was continued for eight days.

A twenty-four hour, 10 liter inoculum prepared as above was aseptically transferred to 130 liter fermentors containing 70 liters of sterile germination medium 2, and 0.31 g./liter of streptamine sulfate suspended in sterile distilled water was added. Aerobic fermentation was carried out at 29° C. for seven days.

Fermentations were terminated by addition of 10 N sulfuric acid to pH 2.0 and filtration using a filter aid to remove mycelia. The filtered broth was adjusted to pH 7.0, and 1.56 g. of oxalic acid per gram of calcium carbonate present in the medium was added to remove calcium. This was allowed to stand overnight, and the clarified broth was decanted and passed over Bio-Rex 70 (weak cation exchanger) resin in the Na+ form using about 14 g. of resin per liter of broth. The column was then washed with distilled water and eluted with 2 N sulfuric acid. All fractions displaying antibiotic activity were combined, neutralized and concentrated under vacuum below 50° C. to the point where salt crystallization became evident (about ⅓ volume). The pH was then adjusted to 10.5, and four volumes of acetone were added to precipitate inorganics which were removed by filtration. The filtrate was adjusted to pH 5.0 with 6 N sulfuric acid, concentrated under vacuum to approximately 1/20 of the original volume and chilled. A white crystalline crop melting over 300° C. was collected by filtration which was found, from its thin layer chromatography properties and its infrared spectrum, to be identical to streptamine sulfate. From two 10 liter fermentations processed as above, a total of 0.7 g. of streptamine sulfate was obtained, and from two 80 liter fermentations, a total of 21 g. of streptamine sulfate was recovered at this step.

The filtrate was further concentrated and 10 volumes of methanol added yielding the first crude antibiotic solid. From two 10 liter fermentations, 7 g. was obtained, and from two 80 liter fermentations, 24 g. was obtained.

For purposes of identifying antibiotic components during purification procedures, chromatographic mobility values obtained on paper chromatography and thin layer chromatography were determined for gentamicin $C_1$, $C_2$ and $C_{1a}$ and for each of the corresponding aminocyclitol analogs prepared as indicated above, where the chromatographic mobility (hereinafter designated C.M.) is expressed as:

$$C.M. = \frac{\text{distance component from origin}}{\text{distance gentamicin } C_1 \text{ from origin}}$$

The chromatography systems used were as follows:

System 1—Whatman No. 1 paper saturated with 0.95 M sulfate-bisulfate and developed in descending fashion in 80% aqueous ethanol+1.5% NaCl and subsequent bioautography using *B. subtilis* as test organism.

System 2—Silica gel F 254 plate developed in lower phase of chloroform(1):methanol(1):concentrated(28%) ammonium hydroxide(1). Components were located with a ninhydrin spray on heating.

The C.M. values of the major antibiotic components of the present invention in comparison with a reference gentamicin complex, all relative to gentamicin $C_1$, are shown in Table I, where the compounds designated Component $C_1$, Component $C_2$ and Component $C_{1a}$ are to be understood to be, respectively, O-[3-deoxy-4-C-methyl-3-methylamino-β-L-arabinopyranosyl(1→6)]-O-[2-amino-6-methylamino-6-C-methyl-2,3,4,6-tetradeoxy-α-D-erythro-glucopyranosyl-(1→4)]-D-streptamine corresponding to gentamicin $C_1$;

O-[3-deoxy-4-C-methyl-3-methylamino-β-L-arabinopyranosyl(1→6)]-O-[2,6-diamino-6-C-methyl-2,3,4,6-tetradeoxy-α-D-erythro-glucopyranosyl-(1→4)]-D-streptamine corresponding to gentamicin $C_2$; and O-[3-deoxy-4-C-methyl-3-methylamino-β-L-arabinopyranosyl(1→6)]-O-[2,6-diamino-2,3,4,6-tetradeoxy-α-D-erythro-glucopyranosyl-(1→4)]-D-streptamine corresponding to gentamicin $C_{1a}$.

TABLE I

|  | C.M. System 1 | C.M. System 2 |
|---|---|---|
| Gentamicin $C_1$ | 1 | 1 |
| Gentamicin $C_2$ | 0.89 | 0.83 |
| Gentamicin $C_{1a}$ | 0.50 | 0.67 |
| Component $C_1$ (Major) | 0.96 | 0.92 |
| Component $C_2$ (Minor) | 0.76 | 0.75 |
| Component $C_{1a}$ (Minor) | 0.50 | 0.61 |

From the 10 liter fermentors, the crude solid (7 g.), which displayed antibacterial activity, was suspended in 200 ml. of methanol and 10 ml. of concentrated (28%) ammonium hydroxide, and the mixture agitated for thirty minutes and filtered. This was repeated two additional times, and the filtrates were combined and concentrated under vacuum yielding a pale yellow oil weighing 0.9 g. The "spent salts" were essentially devoid of antibiotic activity.

The oily base was mixed with 4 g. of silica gel (Davison grade 923, 100–200 mesh) and charged on a silica gel column measuring 1.8×28 cm. The column was prepared as a slurry using the lower phase of isopropyl alcohol(1):chloroform(2):17% aqueous ammonium hydroxide(1). The column was developed with this solvent and 50 ml. fractions collected.

Fractions 8 and 9 contained a single ninhydrin-positive component which yielded 20 mg. as a pale yellow oil on removal of solvent. The mass spectrum of this material, designated Component $C_1$, showed a molecular ion and major fragments each 16 mass units (i.e. one oxygen atom) greater than that obtained from gentamicin $C_1$ as follows: Reference gentamicin $C_1$: M+ 477, 420, 360, 350, 347, 322, 319, 304; Component $C_1$: M+ 493, 436, 376, 366, 363, 338, 335, 320.

This material was converted to its sulfate salt by dissolving in ethanol and adding a few drops of ethanol containing sulfuric acid. The resulting white solid was collected and dried to yield 22 mg. of Component $C_1$, O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine as the di-base.heptasulfate.decahydrate, m.p. 300° C.

Anal. Calcd. for $(C_{21}H_{43}N_5O_8)_2 \cdot 7H_2SO_4 \cdot 10H_2O$: C,27.22; H,6.53; N,7.55; S,12.09. Found: C,27.15: H,6.67; N,7.79; S,12.76.

Also obtained was the corresponding di-base. pentasulfate.tetrahydrate, m.p. >300° C.

Anal. Calcd. for $(C_{21}H_{43}N_5O_8)_2 \cdot 5H_2SO_4 \cdot 4H_2O$: C,32.55; H,6.75; N,9.04; S,10.35. Found: C,32.5; H,6.9; N,9.4; S,9.8.

The corresponding free base has m.p. 119°–123° C., nmr data: pmr δ ($D_2O$)5.87, 5.60 (anomeric H, 2H); 5.22 (exchangeable H, 12H); 3.15, 3.09 ($NCH_3$, 6H); 2.9–4.8 ($CHO$, $CHN$, $CH_2O$, 12H); 1.9–2.6 ($CH_2CH_2$, 4H); 1.72 ppm ($CH_3C$, $CH_3CH$, 6H). Mass spectrum M+ 493, fragments M/e 436, 376, 366, 363, 338, 335, 320, 160, 157, $[\alpha]_D^{25°} = +128.5°$ (0.2% $H_2O$).

Fractions 10–13 yielded a more polar ninhydrin component designated O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-D-streptamine, Component $C_2$, which displayed antibiotic activity, m.p. 115°–119° C., nmr data: pmr δ ($D_2O$) 5.82, 5.56 (anomeric H, 2H); 5.20 (exchangeable H, 13H); 3.09 ($NCH_3$, 3H); 3.0–4.6 ($CHO$, $CHN$, $CH_2O$, 13H); 1.9–2.5 ($CH_2CH_2$, 4H); 1.73 ppm ($CH_3C$, $CH_3CH$, 6H). Mass spectrum (M++1) 480, fragments M/e 436, 366, 362, 349, 338, 321, 320, 160, 143. $[\alpha]_D^{25} = +137.1°$ C. (0.2% $H_2O$). The compound was converted to the di-base.pentasulfate.hexahydrate, m.p. 228°–230° C.

Anal. Calcd. for $(C_{20}H_{41}N_5O_8)_2 \cdot 5H_2SO_4 \cdot 6H_2O$: C,30.85; H,6.73; N,8.99; S,10.29. Found: C,30.5; H,6.5; N,9.0; S,10.1.

Fractions 15–26 yielded a third more polar component displaying antibiotic activity. The mass spectrum of this component showed characteristic sugar peaks corresponding to gentamicin $C_{1a}$ at 129 (purpurosamine) and 160 (garosamine) and is designated O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-D-streptamine, Component $C_{1a}$.

Alternatively, the new Component $C_1$ was isolated as follows: A mixture of crude antibiotic base obtained as above (0.9 g.) was dissolved in 7 ml. of water and the pH adjusted to 4.5 with 1 N sulfuric acid. The solvent was passed over a strong anion exchange column (IRA 401) in the OH− form (bed measurement=0.7×10 cm). The column was eluted with water and the eluate evaporated in vacuo at 35° C. The resulting residue was triturated with 50 ml. of the lower phase of a solvent composed of 17% aqueous ammonium hydroxide:isopropyl alcohol:chloroform (1:1:2). The solvent was decanted and concentrated under vacuum leaving an oily residue weighing 140 mg. The mass spectrum of this material corresponds to that from fractions 8 and 9 above, i.e., M+ 493, 436, 376, 366, 363, 338, 335, 320.

Alternatively, a 4 g. sample of the crude antibiotic salt was dissolved in 50 ml. of water and passed over an anion exchange resin AG1XB (resin bed 1×27 cm.). The antibiotic was eluted with water and all active fractions combined and evaporated under vacuum. Further desalting was carried out on the residue by extraction with methanolic sodium hydroxide. The liberated base was mixed with 7 g. of silica gel and charged on a 50 g. silica gel column. This column was developed with chloroform:methanol:concentrated (28%)ammonium hydroxide (3:4:2) and 25 ml. fractions collected. Early fractions yielded the new less polar Component $C_1$ but admixed with several less polar impurities as evidenced by thin layer chromatography. These fractions were combined and the concentrate charged on a 50 g. silica gel column as above. This column was developed with chloroform:methanol:concentrated(28%)ammonium hydroxide (5:3:1) and 25 ml. fractions collected. Fractions 6–12 contained the desired component free of obvious impurities. On removal of solvent, the resulting oil was converted to the sulfate salt in ethanolic sulfuric acid as previously described yielding 0.124 g. of Component $C_1$ as the di-base.heptasulfate.decahydrate, m.p. >300° C. described above.

By culturing an appropriate aminocyclitol with mutant *Micromonospora purpurea* ATCC 31,119, in germination medium 2 and isolation of the products as described above in Example 1, the following compounds of formula I are similarly prepared:

EXAMPLE 2

O-[3-Deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]epistreptamine, Component $C_1$, (C.M. relative to gentamicin $C_1$: System 1=0.59, System 2=0.63);

O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]epistreptamine, Component $C_2$; and O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]epistreptamine, Component $C_{1a}$, obtained by use of epistreptamine in place of streptamine in the fermentation procedure.

EXAMPLE 3

O-[3-Deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-2,5-dideoxystreptamine, Component $C_1$, (C.M. relative to gentamicin $C_1$: System 1=0.95, System 2=0.98), nmr data: prm δ (D$_2$O) 5.52, 5.42 (anomeric H, 2H); 5.20 (exchangeable H, 10H); 3.00, 2.92 (CH$_3$N, 6H); 1.68, 1.62 (CH$_3$C, CH$_3$CH, 6H); 1.3–4.5 ppm (all other H, 17H). Mass spectrum M+ 461, fragments M/e 404, 344, 334, 331, 306, 303, 288, 160, 157;

O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-2,5-dideoxystreptamine, Component $C_2$, (C.M. relative to gentamicin $C_1$: System 1=0.66, System 2=0.73), mass spectrum of $C_1$ and $C_2$ components M+ 461 and 447, fragments M/e 404, 344, 334, 331, 330, 317, 306, 303, 289, 288, 160, 157, 143; and O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-2,5-dideoxystreptamine, Component $C_{1a}$, obtained by use of dideoxystreptamine in place of streptamine in the fermentation procedure. nmr data for the $C_{1a}$ component: pmr δ (D$_2$O) 5.52, 5.44 (anomeric H, 2H): 5.20 (exchangeable H, 11H); 3.00 (CH$_3$N, 3H); 1.67 (CH$_3$C, 3H); 1.3–4.5 ppm (all other H, 19H). Mass spectrum M+ 433, fragments M/e 334, 316, 306, 303, 288, 275, 160, 129.

The same O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-2,5-dideoxystreptamine, Component $C_1$; and O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-2,5-dideoxystreptamine, Component $C_2$, described above and having the same C.M. values as given above were obtained by use of 6,7-diazabicyclo-[3.2.1]octane-2,4-diol (exo, exo) in place of streptamine in the fermentation procedure.

EXAMPLE 4

Following a procedure similar to that described in Example 1, it is contemplated that O-[3-Deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl(1→4)]-5-iodo-2,5-dideoxystreptamine, Component $C_1$;

O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-5-iodo-2,5-dideoxystreptamine, Component $C_2$; and O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-5-iodo-2,5-dideoxystreptamine, Component $C_{1a}$, obtained by use of 5-iodo-2,5-dideoxystreptamine in place of streptamine in the fermentation procedure.

EXAMPLE 5

Following a procedure similar to that described in Example 1, it is contemplated that O-[3-Deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-5-fluoro-2,5-dideoxystreptamine, Component $C_1$;

O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-5-fluoro-2,5-dideoxystreptamine, Component $C_2$; and O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-5-fluoro-2,5-dideoxystreptamine, Component $C_{1a}$, can be obtained by use of 5-fluoro-2,5-dideoxystreptamine in place of streptamine in the fermentation procedure.

SYNTHESIS OF AMINO-HYDROXY-LOWER-ALKANOYL DERIVATIVES

EXAMPLE 6

A solution of 270 mg. (0.54 millimole) of O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine, described above in Example 1 (Component $C_1$), dissolved in 5 ml. of 50% aqueous tetrahydrofuran was cooled to 5° C. in an ice bath and treated with 208 mg. (0.59 millimole) of the N-hydroxysuccinimide ester of S-(—)-γ-(N-benzyloxycarbonyl)amino-α-hydroxybutyric acid (Konishi et al. U.S. Pat. No. 3,780,018), and the mixture was stirred at 5° C. for twenty hours. The mixture was then concentrated to 10 ml. in vacuo. n-Butanol (25 ml.) and water (10 ml.) were added, and the layers were separated. The aqueous layer was washed again with 10 ml. of n-butanol. The combined organic layers were evaporated leaving a residue of 513 mg. of crude product which was set aside.

The aqueous layer was evaporated to dryness to give 304 mg. of residue which was dissolved in 25 ml. of 50% aqueous tetrahydrofuran and treated with an additional 208 mg. of the N-hydroxysuccinimide ester of S-(—)-γ-(N-benzyloxycarbonyl)amino-α-hydroxybutyric acid as before. Work up of the reaction mixture afforded an additional 435 mg. of crude product which was combined with the 513 mg. previously obtained and chromatographed on seven 40×20 cm. silica gel plates 1 mm. thick. The system was developed with chloroform:methanol:concentrated(28%)ammonium hydroxide (3:1:1) (lower phase). Seven passes in this solvent system were necessary, and after eluting the product band which was ultraviolet visible, 229.5 mg. of a crude mixture of the three monoacylated products was obtained.

The mixture of acylated products was put on three 40×20 cm. silica gel plates 1 mm. thick and the plates developed five times with chloroform:isopropanol:concentrated(28%)ammonium hydroxide (4:1:1) (lower phase), twice with chloroform:isopropanol:concentrated(28%)ammonium hydroxide (3:1:1) (lower phase) and nine times with chloroform:methanol:concentrated(28%)ammonium hydroxide (4:1:1) (lower phase). Three distinct bands visible under ultraviolet irradiation were obtained which were separately cut out and eluted from the silica gel with chloroform:methanol:concentrated(28%)ammonium hydroxide (1:1:1) (lower phase) affording three components: A, 90.9 mg.; B, 59.1 mg.; and C, 48.5 mg., which are the S-(—)-γ-(N-benzyloxycarbonyl)amino-α-hydroxybutyric acid amide derivatives at the 2'-, 1- and 3-positions, respectively, of O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine (Component $C_1$). The $R_f$ values for components A, B and C, when developed five times on silica gel with a chloroform:methanol:concentrated(28%)ammonium hydroxide (4:1:1) (lower phase) system, were:

A—0.48
B—0.62
C—0.70.

Component B (the 1-amide, 56.1 mg.) dissolved in 25 ml. of 50% aqueous ethanol and 20 mg. of 10% palladium-on-charcoal was shaken in a Parr shaker at 55 p.s.i. for five and a half hours after which time the catalyst was removed by filtration through filter aid. Evaporation of the solvent afforded 34.3 mg. of a white glass which was dissolved in 2.5 ml. of water and treated with 11.4 mg. of sulfuric acid in 0.1 ml. of water. Addition of 10 ml. of ethanol precipitated 1-[S-(—)-γ-amino-α-hydroxybutyryl]-O-[3-deoxy-4-C-methyl-3-methylamino-β-L-arabinopyranosyl-(1→6)]-O-[2-amino-6-methyl-amino-6-C-methyl-2,3,4,6-tetradeoxy-α-D-erythro-glucopyranosyl-(1→4)]-D-streptamine as the pentasulfate salt (32 mg.), m.p. 230°–235° C. (decomp.); tlc, $R_f$=0.18 (silica gel, chloroform:methanol:concentrated(28%)ammonium hydroxide:water, 1:4:2:1; $R_f$ gentamicin $C_1$ standard=0.73).

Anal. Calcd. for $C_{25}H_{50}O_{10}N_6 \cdot 5H_2SO_4$: C,27.67;H,5.57; N,7.75. Found: C,27.50;H,5.58; N,7.42.

Components A and C were treated in a similar fashion. A afforded 47 mg. of 2'-[S-(—)-γ-amino-α-hydroxybutyryl]-O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine as the bisbase.tetrasulfate.heptahydrate, m.p. 237°–241° C. (decomp.); tlc, $R_f$=0.33 [silica gel, chloroform:methanol:concentrated(28%)ammonium hydroxide:water, 1:4:2:1; $R_f$ gentamicin $C_1$ standard=0.73].

Anal. Calcd. for $(C_{25}H_{50}N_6O_{10})_2 \cdot 4H_2SO_4 \cdot 7H_2O$: C,35.16;H,7.20;N,9.84. Found: C,35.38;H,7.08;N,9.49.

Component C afforded 26 mg. of 3-[S-(—)-γ-amino-α-hydroxybutyryl]-O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine as the bis-base.pentasulfate.trihydrate, m.p. 220°–230° C. (decomp.); tlc, $R_f$=0.30 [silica gel, chloroform:methanol:concentrated(28%)ammonium hydroxide:water, 1:4:2:1; $R_f$ gentamicin $C_1$ standard=0.73].

Anal. Calcd. for $(C_{25}H_{50}N_6O_{10})_2 \cdot 5H_2SO_4 \cdot 3H_2O$: C,34.64;H,6.74;N,9.67. Found: C,34.35;H,6.38;N,8.60.

Proceeding in a manner similar to that described in Example 6 using the respective antibiotics described in Examples 2, 3, 4 and 5 and either the N-hydroxysuccinimide ester of S-(—)-γ-(N-benzyloxycarbonyl)amino-α-hydroxybutyric acid or the pentafluorophenyl ester of N-(benzyloxycarbonyl)(S)-isoserine [(S)-β-amino-α-hydroxypropionic acid], described by Haskell et al., Carbohydrate Research, 28, 263–280 (1973), it is contemplated that the following compounds of formula I can be similarly prepared:

EXAMPLE 7

1-[(S)-β-Amino-α-hydroxypropionyl]-O-[3-deoxy-4-C-methyl-3-methylamino-β-L-arabinopyranosyl-(1→6)]-O-[2,6-diamino-6-C-methyl-2,3,4,6-tetradeoxy-α-D-erythroglucopyranosyl-(1→4)]epistreptamine and 2'-[(S)-β-amino-α-hydroxypropionyl]-O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]epistreptamine.

EXAMPLE 8

1-[S-(—)-γ-Amino-α-hydroxybutyryl]-O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-2,5-dideoxystreptamine and 2'-[S-(—)-γ-amino-α-hydroxybutyryl]-O-[3- deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-2,5-dideoxystreptamine.

EXAMPLE 9

1-[(S)-β-Amino-α-hydroxypropionyl]-O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-5-iodo-2,5-dideoxystreptamine and 2'-[(S)-β-amino-α-hydroxypropionyl]-O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-5-iodo-2,5-dideoxystreptamine.

EXAMPLE 10

1-[S-(−)-γ-Amino-α-hydroxybutyryl]-O-[3-deoxy-4-C-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-5-fluoro-2,5-dideoxystreptamine and 2'-[S-(−)-γ-amino-α-hydroxybutyryl]-O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-5-fluoro-2,5-dideoxystreptamine.

Antibacterial Test Results

The O-[3-deoxy-4-C-methyl-3-methylamino-β-L-arabinopyranosyl-(1→6)]-O-[2-amino-6-methylamino-6-C-methyl-2,3,5,6-tetradeoxy-α-D-erythro-glucopyranosyl-(1→4)]-D-streptamine and O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-2,5-dideoxystreptamine (Component $C_1$ or Deoxy-$C_1$); O-[3-deoxy-4-C-methyl-3-methylamino-β-L-arabinopyranosyl-(1→6)]-O-[2,6-diamino-6-C-methyl-2,3,4,6-tetradeoxy-α-D-erythro-glucopyranosyl-(1→4)]-2,5-dideoxystreptamine (Component $C_2$ or Deoxy-$C_2$); and O-[3-deoxy-4-C-methyl-3-methylamino-β-L-arabinopyranosyl-(1→6)]-O-[2,6-diamino-2,3,4,6-tetradeoxy-α-D-erythro-glucopyranosyl-(1→4)]-2,5-dideoxystreptamine described above in Example 3, identified in Table II below as Deoxy-$C_1$+$C_2$+$C_{1a}$ as well as the pure $C_1$ component, identified in Table II as Deoxy-$C_1$.

Stock solutions of each compound, containing 200 mcg./ml. base were prepared in distilled water and filter sterilized. Cultures of the test organisms were grown for twenty-four hours at 37° C. in 10 ml. tubes of tryptose phosphate or Mueller-Hinton broth. Each culture was adjusted with broth to 0.1 optical density on a Spectronic 20 (approximately $10^8$ cells/ml.). The adjusted cultures were diluted 1:500 in broth for use as inoculum (final cell concentration approximately $2 \times 10^5$ cells/ml.). The test compounds were tested for antibacterial activity by a single-row tube dilution method. Master two-fold serial dilutions were made in broth from the stock drug solutions, and 0.2 ml. of each drug concentration was placed in seventeen 13×100 mm. tubes. All tubes were inoculated with 0.2 ml. of the appropriate diluted culture (final cell concentration per tube = $10^5$ cells/ml.). Minimum inhibitory concentrations (lowest drug concentration showing no visible growth) were read after sixteen hours incubation at 37° C.

The results are given in Table II below. The compounds were considered inactive at inhibitory concentrations greater than 100 mcg./ml.

TABLE II

| | Minimum Inhibitory Conc. (mcg./ml.) | | | | | | | |
|---|---|---|---|---|---|---|---|---|
| Organism | Oxy-$C_1$ | Oxy-$C_2$ | Oxy-$C_1$ + $C_2$ | G—$C_1$ + $C_2$ + $C_{1a}$ | G—$C_1$ | G—$C_2$ | Deoxy-$C_1$ + $C_2$ + $C_{1a}$ | Deoxy-$C_1$ |
| S. aureus Smith | 0.78 | 0.39 | 0.78 | 0.39 | 0.39 | 0.2 | 0.195 | 0.195 |
| E. coli Vogel | 3.13 | 3.13 | 3.13 | 3.13 | 3.13 | 1.56 | 1.56 | 1.56 |
| E. coli W677/HJR66 | 50 | 100 | 50 | >100 | >100 | >100 | — | — |
| E. coli JR35 | 3.13 | 1.56 | 1.56 | 1.56 | 3.13 | 1.56 | — | — |
| E. coli JR76.2 | 6.25 | 12.5 | 6.25 | 50 | 50 | 50 | 50 | 50 |
| E. coli JR89 | 100 | 50 | 25 | 50 | 100 | 50 | 6.25 | 12.5 |
| E. coli K12ML1629 | 3.13 | 1.56 | 1.56 | 1.56 | 1.56 | 1.56 | — | — |
| Ent. cloacae A-20960 | 3.13 | 6.25 | 3.13 | 25 | 25 | 25 | 25 | 12.5 |
| K. pneumoniae A-20636 | 6.25 | 6.25 | 6.25 | 25 | 50 | 50 | 25 | 25 |
| K. pneumoniae 39645 | 3.13 | 1.56 | 3.13 | 1.56 | 1.56 | 0.78 | 0.78 | 0.78 |
| Pr. mirabilis MGH-1 | 6.25 | 1.56 | 6.25 | 1.56 | 1.56 | 1.56 | 1.56 | 0.78 |
| Prov. stuartii A-20894 | >100 | 50 | 100 | >100 | >100 | 100 | 25 | 50 |
| Providencia 164 | >100 | 25 | 50 | 100 | >100 | 50 | 12.5 | 25 |
| Ps. aeruginosa A-20897 | 50 | >100 | 50 | 100 | >100 | >100 | 12.5 | 6.25 |
| Ps. aeruginosa A-20741 | >100 | >100 | — | 100 | >100 | >100 | 100 | 100 |
| Ps. aeruginosa MGH-2 | 6.25 | 3.13 | 1.56 | 0.39 | 3.13 | 1.56 | 0.78 | 1.56 |
| Ps. aeruginosa C | 6.25 | 3.13 | — | — | 3.13 | 1.56 | — | — |
| Ps. aeruginosa #2 | 6.25 | 1.56 | — | — | 1.56 | 0.78 | — | — |

(a)Cultured in tryptose phosphate broth

α-D-erythro-glucopyranosyl-(1→4)]-D-streptamine described above in Example 1 and designated Components $C_1$ and $C_2$, respectively, were tested both as the individual pure components (Oxy-$C_1$ and Oxy-$C_2$) or combined components (Oxy-$C_1$+$C_2$) in comparison with gentamicin complex $C_1$, $C_2$, $C_{1a}$ (G-$C_1$+$C_2$+$C_{1a}$) and gentamicin components $C_1$ and $C_2$ (G-$C_1$ and G-$C_2$) against a number of microorganisms according to the procedure described below. Also tested were the $C_1$, $C_2$, $C_{1a}$ complex of O-[3-deoxy-4-C-methyl-3-methylamino-β-L-arabinopyranosyl-(1→6)]-O-[2-amino-6-methylamino-6-C-methyl-2,3,4,6-tetradeoxy- The same Component $C_1$ described above in Example 1, O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine, was tested in comparison with gentamicin complex ($C_1$, $C_2$ and $C_{1a}$) and gentamicin $C_1$, and the 1-, 3- and 2'-[S-(−)-γ-amino-α-hydroxybutyryl]amides of Component $C_1$, described above in Example 8, and designated, respectively, Component $C_1$ (1-HABA), Component $C_1$ (3-HABA) and Component $C_1$ (2'-HABA), were tested in comparison with the corresponding 1-, 3- and 2'-[S-(−)-γ-amino-α-hydroxybutyryl]amides of gentamicin $C_1$ (all described by Konishi et al. U.S. Pat. No. 3,780,018, patented Dec. 18, 1973) and designated, respectively, $C_1$ (1HABA), $C_1$ (3-HABA) and $C_1$ (2'-HABA). These results are given in Table III below where test organisms 1, 2, 3, 4, 5 and 6 identify B. subtilis ATCC 6633, S. aureus Smith, E. coli JR 76.2, Ent. cloacae A-20960, K. pneumoniae A-20636 and Ps. aeruginosa A-20897, respectively.

TABLE III

| Compound | Test Organisms | | | | | |
|---|---|---|---|---|---|---|
| | 1 | 2 | 3 | 4 | 5 | 6 |
| Gentamicin $C_1$, $C_2$, $C_{1a}$ | <0.024 | 0.39 | 50 | 12.5 | 25 | >100 |
| Gentamicin $C_1$ | 0.049 | 0.78 | 50 | 12.5 | 25 | >100 |
| Component $C_1$ | 0.098 | 1.56 | 6.25 | 0.78 | 3.13 | 25 |
| $C_1$ (1-HABA) | 0.39 | 3.13 | 12.5 | 3.13 | 6.25 | >100 |
| Component $C_1$ (1-HABA) | 0.78 | 6.25 | 12.5 | 6.25 | 12.5 | >100 |
| $C_1$ (3-HABA) | 3.13 | 25 | >100 | 100 | >100 | >100 |
| Component $C_1$ (3-HABA) | 6.25 | 50 | 100 | 50 | 50 | >100 |
| $C_1$ (2'-HABA) | 6.25 | 50 | 100 | 25 | 50 | >100 |
| Component $C_1$ (2'-HABA) | 1.56 | 25 | 50 | 25 | 50 | >100 |

(b)Cultured in Mueller-Hinton broth.

We claim:
1. A compound having the formula:

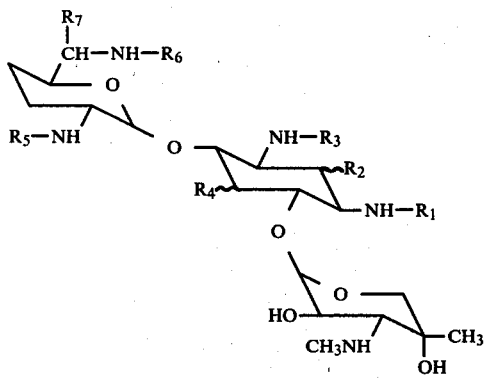

where $R_1$, $R_3$ and $R_5$ each represent hydrogen, or one of $R_1$, $R_3$ and $R_5$ represents an ω-amino-α-hydroxy-lower-alkanoyl group having the formula:

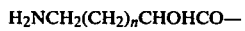

$H_2NCH_2(CH_2)_nCHOHCO-$ where n is zero or 1, the other of $R_1$, $R_3$ and $R_5$ being hydrogen; $R_2$ represents hydrogen or hydroxy; $R_4$ represents hydrogen, hydroxy or halogen, except that when $R_2$ is hydrogen, $R_4$ is not hydroxy; and $R_6$ and $R_7$ each represent hydrogen or methyl.

2. A compound according to claim 1 where $R_1$, $R_3$ and $R_5$ each represent hydrogen.

3. A compound according to claim 1 where one of $R_1$, $R_3$ and $R_5$ represents an ω-amino-α-hydroxy-lower-alkanoyl group having the formula:

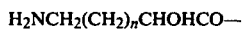

$H_2NCH_2(CH_2)_nCHOHCO-$ where n is zero or 1, the other of $R_1$, $R_3$ and $R_5$ being hydrogen.

4. A compound according to claim 3 where $R_2$ and $R_4$ each represent hydroxy.

5. O-[3-Deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine according to claim 2.

6. O-3-Deoxy-4-C-methyl-3-methylamino-β-L-arabinopyranosyl-(1→6)-O-[2,6-diamino-6-C-methyl-2,3,4,6-tetradeoxy-α-D-erythro-glucopyranosyl-(1→4)]-D-streptamine according to claim 2.

7. O-3-Deoxy-4-C-methyl-3-methylamino-β-L-arabinopyranosyl-(1→6)-O-[2,6-diamino-2,3,4,6-tetradeoxy-α-D-erythro-glucopyranosyl-(1→4)]-D-streptamine according to claim 2.

8. O-3-Deoxy-4-C-methyl-3-methylamino-β-L-arabinopyranosyl-(1→6)-O-[2-amino-6-methylamino-6-C-methyl-2,3,4,6-tetradeoxy-α-D-erythro-glucopyranosyl-(1→4)]-2,5-dideoxystreptamine according to claim 2.

9. O-3-Deoxy-4-C-methyl-3-methylamino-β-L-arabinopyranosyl-(1→6)-O-[2,6-diamino-6-C-methyl-2,3,4,6-tetradeoxy-α-D-erythro-glucopyranosyl-(1→4)]-2,5-dideoxystreptamine according to claim 2.

10. O-3-Deoxy-4-C-methyl-3-methylamino-β-L-arabinopyranosyl-(1→6)-O-[2,6-diamino-2,3,4,6-tetradeoxy-α-D-erythro-glucopyranosyl-(1→4)]-2,5-dideoxystreptamine according to claim 2.

11. 2'-[S-(−)-γ-Amino-α-hydroxybutyryl]-O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine according to claim 4.

12. 1-[S-(−)-γ-Amino-α-hydroxybutyryl]-O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine according to claim 4.

13. 3-[S-(−)-γ-Amino-α-hydroxybutyryl]-O-[3-deoxy-4-C-methyl-3-methylamino-β-L-arabinopyranosyl-(1→6)]-O-[2-amino-6-methylamino-6-C-methyl-2,3,4,6-tetradeoxy-α-D-erythro-glucopyranosyl-(1→4)]-D-streptamine according to claim 4.

14. A 5-deoxy-4,6-di-O-(aminoglycosyl)-1,3-diaminocyclitol selected from the group consisting of 5-deoxygentamicin $C_{1a}$, 5-deoxygentamicin $C_2$, the 1-N-X derivatives thereof wherein X is $$-\overset{O}{\underset{\|}{C}}-Z,$$

wherein Z is aminohydroxyalkyl, said substituent Z having up to 3 carbon atoms and, when substituted by amino and hydroxy, bearing the substituents on different carbon atoms; and the pharmaceutically acceptable acid addition salts thereof.

15. A compound of claim 14 which is a 4-O-aminoglycosyl-6-O-garosaminyl-2,5-dideoxystreptamine.

16. A compound of claim 15 which is 5-deoxygentamicin $C_2$.

17. A compound of claim 14 which is 1-N-X-4-O-aminoglycosyl-6-O-garosaminyl-2,5-dideoxystreptamine wherein X is 4-amino-2-hydroxybutyryl.

18. The method of eliciting an antibacterial response in a warm-blooded animal having a susceptible bacterial infection which comprises administering to said animal a non-toxic, antibacterially effective amount of a member selected from the group consisting of a 5-deoxy-4,6- di-O-(aminoglycosyl)-1,3-diaminocyclitol selected from the group consisting of
5-deoxygentamicin $C_{1a}$,
5-deoxygentamicin $C_2$,
the 1N-X derivatives thereof wherein X is a substituent selected from the group consisting of

wherein Z is aminohydroxyalkyl, said substituent Z having up to 3 carbon atoms and, when substituted by amino and hydroxy, bearing the substituents on different carbon atoms; and the pharmaceutically acceptable acid addition salts thereof.

19. A pharmaceutical composition comprising an antibacterially effective amount of a member selected from the group consisting of a 5-deoxy-4,6-di-O-(aminoglycosyl)-1,3-diaminocyclitol selected from the group consisting of
5-deoxygentamicin $C_{1a}$,
5-deoxygentamicin $C_2$,
the 1-N-X derivatives thereof wherein X is a substituent selected from the group consisting of

wherein Z is aminohydroxyalkyl, said substituent Z having up to 3 carbon atoms and, when substituted by amino and hydroxy, bearing the substituents on different carbon atoms; and the pharmaceutically acceptable acid addition salts thereof; together with a non-toxic pharmaceutically acceptable carrier.

20. A compound of claim 14 which is a 1-N-X-4-O-aminoglycosyl-6-O-garosaminyl-2,5-dideoxystreptamine wherein X is 3-amino-2-hydroxypropionyl or 4-amino-2-hydroxybutyryl.

21. A compound according to claim 1 wherein $R_1$, $R_2$, $R_3$, $R_4$ and $R_5$ each represent hydrogen.

22. A compound according to claim 1 where $R_3$ and $R_5$ each represent hydrogen and $R_1$ represents an $\omega$-amino-$\alpha$-hydroxy-lower-alkanoyl group having the formula:

$$H_2NCH_2(CH_2)_nCHOHCO-$$

where n is 0 or 1.

23. The method of eliciting an antibacterial response in a warm-blooded animal having a susceptible bacterial infection which comprises administering to said animal a non-toxic antibacterially effective amount of a compound of claim 1.

24. A pharmaceutical composition comprising an antibacterially effective amount of a compound of claim 1, together with a non-toxic pharmaceutically acceptable carrier.

* * * * *